(12) United States Patent
Ward et al.

(10) Patent No.: US 10,307,288 B2
(45) Date of Patent: Jun. 4, 2019

(54) METHODS AND APPARATUS FOR OPTIMIZING THERAPEUTIC TEMPERATURE CONTROL

(71) Applicants: Hasan Alam, Ann Arbor, MI (US); Kevin Ward, Superior Township, MI (US); Kyle Gunnerson, Saline, MI (US); Kayvan Najarian, Northville, MI (US)

(72) Inventors: Kevin Ward, Superior Township, MI (US); Kyle Gunnerson, Saline, MI (US); Kayvan Najarian, Northville, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 122 days.

(21) Appl. No.: 15/307,690

(22) PCT Filed: Apr. 29, 2015

(86) PCT No.: PCT/US2015/028188
§ 371 (c)(1),
(2) Date: Oct. 28, 2016

(87) PCT Pub. No.: WO2015/168228
PCT Pub. Date: Nov. 5, 2015

(65) Prior Publication Data
US 2017/0049618 A1   Feb. 23, 2017

Related U.S. Application Data

(60) Provisional application No. 62/083,086, filed on Nov. 21, 2014, provisional application No. 61/985,860, filed on Apr. 29, 2014.

(51) Int. Cl.
*A61B 5/00* (2006.01)
*A61B 5/01* (2006.01)
(Continued)

(52) U.S. Cl.
CPC ............... *A61F 7/12* (2013.01); *A61B 3/113* (2013.01); *A61B 5/01* (2013.01); *A61B 5/02055* (2013.01);
(Continued)

(58) Field of Classification Search
CPC ... A61F 7/12; A61B 3/113; A61B 5/01; A61B 5/02055; A61B 5/0476; A61B 5/14542; A61B 5/14551
(Continued)

(56) References Cited

U.S. PATENT DOCUMENTS 8,491,644 B1 * 7/2013 Carson ..................... A61F 7/02
                                                      607/104
2007/0203552 A1 * 8/2007 Machold ............... A61M 25/10
                                                      607/104
(Continued)

OTHER PUBLICATIONS

International Search Report and Written Opinion for Application No. PCT/US2015/028188, dated Aug. 19, 2015.

*Primary Examiner* — Phillip A Gray
(74) *Attorney, Agent, or Firm* — Marshall, Gerstein & Borun LLP

(57) ABSTRACT

Vascular pressures and oximetry are optimized through administration of fluids and other support prior to manipulating temperature in a therapeutic hypothermia procedure. Temperature and active hemodynamic management are utilized, through measurement and adjustment of temperature and hemodynamic parameters through the use of an internal cooling device, such as endovascular catheter, and/or an external temperature-altering device, to ensure that temperature management is optimized, and hemodynamics and tissue resuscitation are optimized prior to and during temperature manipulation.

19 Claims, 5 Drawing Sheets

(51) Int. Cl.
*A61B 5/08* (2006.01)
*A61F 7/12* (2006.01)
*A61B 5/0205* (2006.01)
*A61B 5/0476* (2006.01)
*A61B 5/1455* (2006.01)
*A61F 7/02* (2006.01)
*A61B 3/113* (2006.01)
*A61B 5/145* (2006.01)
*A61F 7/08* (2006.01)
*A61M 5/142* (2006.01)
*A61B 5/021* (2006.01)
*A61B 5/024* (2006.01)
*A61F 7/00* (2006.01)
*A61B 5/0484* (2006.01)
*A61B 5/053* (2006.01)

(52) U.S. Cl.
CPC ........ *A61B 5/0476* (2013.01); *A61B 5/14542* (2013.01); *A61B 5/14551* (2013.01); *A61B 5/4836* (2013.01); *A61B 5/6852* (2013.01); *A61B 5/7267* (2013.01); *A61F 7/02* (2013.01); *A61F 7/08* (2013.01); *A61M 5/142* (2013.01); *A61B 5/021* (2013.01); *A61B 5/02405* (2013.01); *A61B 5/0484* (2013.01); *A61B 5/0533* (2013.01); *A61B 5/0816* (2013.01); *A61B 5/412* (2013.01); *A61B 2505/01* (2013.01); *A61F 2007/0093* (2013.01); *A61F 2007/0094* (2013.01); *A61F 2007/0096* (2013.01); *A61F 2007/126* (2013.01)

(58) Field of Classification Search
USPC .......................................................... 604/113
See application file for complete search history.

(56) References Cited

U.S. PATENT DOCUMENTS

| | | |
|---|---|---|
| 2008/0071337 A1 | 3/2008 | Dobak et al. |
| 2009/0043366 A1 | 2/2009 | Dae |
| 2009/0131835 A1 | 5/2009 | Voorhees et al. |
| 2010/0100144 A1 | 4/2010 | Shuros et al. |
| 2011/0238020 A1 | 9/2011 | Goedje et al. |
| 2013/0331916 A1 | 12/2013 | Pile-Spellman et al. |

\* cited by examiner

METHODS AND APPARATUS FOR OPTIMIZING THERAPEUTIC TEMPERATURE CONTROL

CROSS-REFERENCE TO RELATED APPLICATIONS

The present application is the US national phase of International Patent Application No. PCT/US2015/028188, filed Apr. 29, 2015, which application claims the benefit of the filing dates of U.S. Provisional Application Nos. 61/985,860, filed Apr. 29, 2014, and 62/083,086, filed Nov. 21, 2014. The priority applications, U.S. Provisional Application Nos. 61/985,860 and 62/083,086, are hereby incorporated by reference.

FIELD OF THE DISCLOSURE

The present disclosure is generally directed to the field of therapeutic hypothermia (TH) for the treatment of such disorders as post-resuscitation syndrome after cardiac arrest, spinal cord injury, myocardial infarction, stroke, traumatic brain injury, trauma, sepsis, and cardiogenic shock.

BACKGROUND

Hypothermia is a condition in which body temperature is at a level lower than normal body temperature. Hypothermia can be endogenous or exogenous. Endogenous hypothermia occurs because heat produced by normal metabolism is reduced due to conditions such as hypoperfusion of tissues which limit the delivery of oxygen and nutrients necessary for cells to metabolize and thus produce heat. Exogenous hypothermia occurs when external factors create a temperature gradient which promotes more heat loss or transfer from the body to the environment than the metabolism can compensate for. The external factors can include the ambient environment around the body or it can include the provision of hypothermic stimuli into the body such as cold intravenous fluids or intravascular devices which create the heating gradient. Hyperthemia follows these same general principals but in a reverse fashion.

Therapeutic hypothermia (TH) is now a well-developed technique used in certain surgeries where blood flow to the brain may be jeopardized and in the post resuscitation care of the victim of cardiac arrest. In both settings, this is done to help preserve or improve neurologic function. Hypothermia can be induced by both external and internal means, as well as combinations of external and internal means. For example, cooling pads applied to the body surface can be used to lower body temperature by cooling from the exterior surface of the patient. Cooling can also be achieved by immersing the patient in cool water or exposing them to cool air, for example. Often times it is desirable to cool the body very quickly, and this can be achieved by an internal means referred to as endovascular cooling. In operation, heat is removed from the blood using a catheter (an endovascular cooling catheter) such that blood flowing across the surface of the cooled catheter transfers heat, and blood of reduced temperature then flows throughout the body to cool the body and its vital organs. Providing therapeutic warming is simply done the same way except that the external or internal means transfers heat into the body.

Despite the routine use of TH, little is known concerning what the optimal temperature is that will result in the most favorable outcome. Currently, most devices allow targeting of a temperature and utilize a temperature feedback control scheme to permit closed loop control of cooling and heating. For this, endovascular temperature modulating catheters are placed in either the inferior or superior vena cava.

U.S. Patent Publication 2009/0131835 to Voorhees describes a patient temperature response control system used in TH. In operation, the Voorhees system utilizes a variety of sensors (motion sensors, vasoconstriction sensors, electomusculature sensors, carbon dioxide sensors, and blood oxygen sensors) to monitor the patient to detect a physiologic response of a patient (such as shivering) to a change in temperature of the patient, and to control temperature and the delivery of anti-shivering medication.

U.S. Patent Publication 2009/0043366 to Dae describes using endovascular cooling to treat septic shock and other disorders. Dae shows measurement of a variety of patient parameters with manipulation of patient temperature.

Neither Voorhees nor Dae permit a true optimization because their feedback loops are designed solely for manipulation of temperature and not other variables by a single system. Thus, depending on a number of factors, the patient may be cooled inappropriately. Further, with these devices the patient cannot be simultaneously resuscitated in a closed loop fashion.

Such ability is critical to ensure the appropriate application of cooling or warming to the body. For example, providing hypothermia to a patient who is not well resuscitated and is hypoperfused may cause significant life threatening complications such as coagulopathy.

SUMMARY

The methodology described herein makes significant improvements to current endovascular cooling catheters, and other internal and external devices or methodologies for therapeutically altering patient temperature, by allowing for targeting of therapeutic hypothermia, normothermnia, or hyperthermia to what may be more useful physiological endpoints. In addition, the improvements allow for simultaneous targeting of hemodynamic variables in a goal directed manner. This is referred to herein as Goal Directed Therapy (GDT).

According to an exemplary embodiment of the present disclosure, vascular pressures and oximetry are optimized through giving of fluids and other support prior to manipulating temperature in a TH procedure.

The present disclosure utilizes both temperature and active hemodynamic management to ensure that temperature management is optimized. The approach ensures hemodynamics and tissue resuscitation are optimized prior to or during the time temperature is being manipulated.

DETAILED DESCRIPTION

We advocate a combined hemodynamic-metabolic and temperature goal directed (or personalized) management system for the resuscitation of patients with critical illness and injury. An example of this would be the incorporation of oximetric and other measurement capabilities into the distal end of endovascular temperature catheters allowing for the measurement of venous hemoglobin oxygen saturation. This is shown generally in FIG. 1 as a cooling platform system where the catheter 10 is associated with one or more sensors 12, 12' which provide output to a control device 14 (one or more controllers or computers, etc.) either by wired or wireless connection. Oximetric capabilities could be accomplished, for example, by using a number of optical techniques and embedded fibers based on near infrared absorption spectroscopy, resonance Raman spectroscopy or other spectroscopic techniques. Furthermore, the oximetric values coming from the endovascular catheter 10 could be coupled with arterial oxygen saturation data provided by an external pulse oximeter (not shown) or indwelling arterial catheter capable of continuous blood gas measurements (not shown). These values are used together in the cooling/warming platform system to determine an oxygen extraction ratio (OER). The cooling/warming platform system controlling the catheter 10 temperature may house the pulse oximeter or it may take pulse oximetry from an external device.

Figure 2:
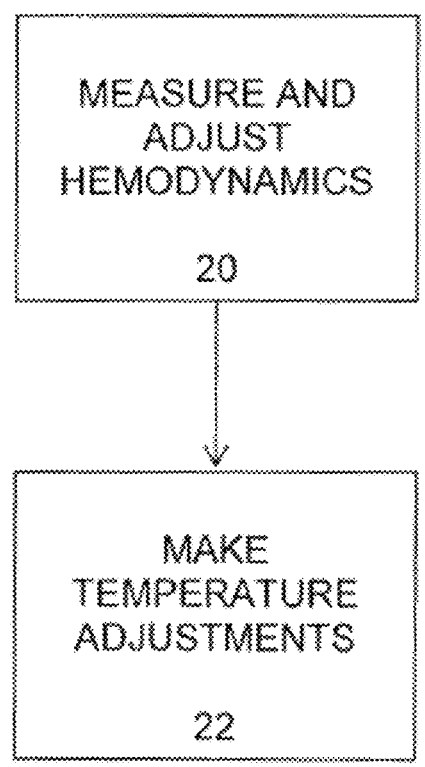
FIG. 2 is a generalized flow diagram showing prior optimization of hemodynamics before temperature manipulation and simultaneous optimization of hemodynamics during temperature manipulation.

OER is a measure of metabolism and is a surrogate for the balance of oxygen consumption and delivery, and as such can be used as a target for therapeutic temperature manipulation. Thus it can be used to tailor therapeutic temperature control to each patient individually, meaning that some patients may need to be cooled or warmed to different temperatures to obtain a therapeutic effect as opposed to targeting a single temperature or range of temperatures for a plurality of patients. This can be considered as a more physiological approach. FIG. 2 shows schematically that one first measures and adjusts the patient's hemodynamics 20 prior to or simultaneous to making temperature adjustments 22 with the catheter. This method may be particularly helpful in cases of trauma, sepsis, or other global perfusion abnormalities where oxygen consumption is also linked to coagulation and inflammatory responses. Additionally, this approach will identify individuals who are hypothermic due to hypoperfusion and thus experiencing reduced oxygen consumption. Therapeutic hypothermia (TH) in these individuals is likely to be harmful. Correction of perfusion abnormalities using the goal directed properties of the technology prior to or during TH should improve the effects of subsequent TH. Technologies other than endovascular cooling and heating may be used including those used for surface cooling and heating.

Figure 1:
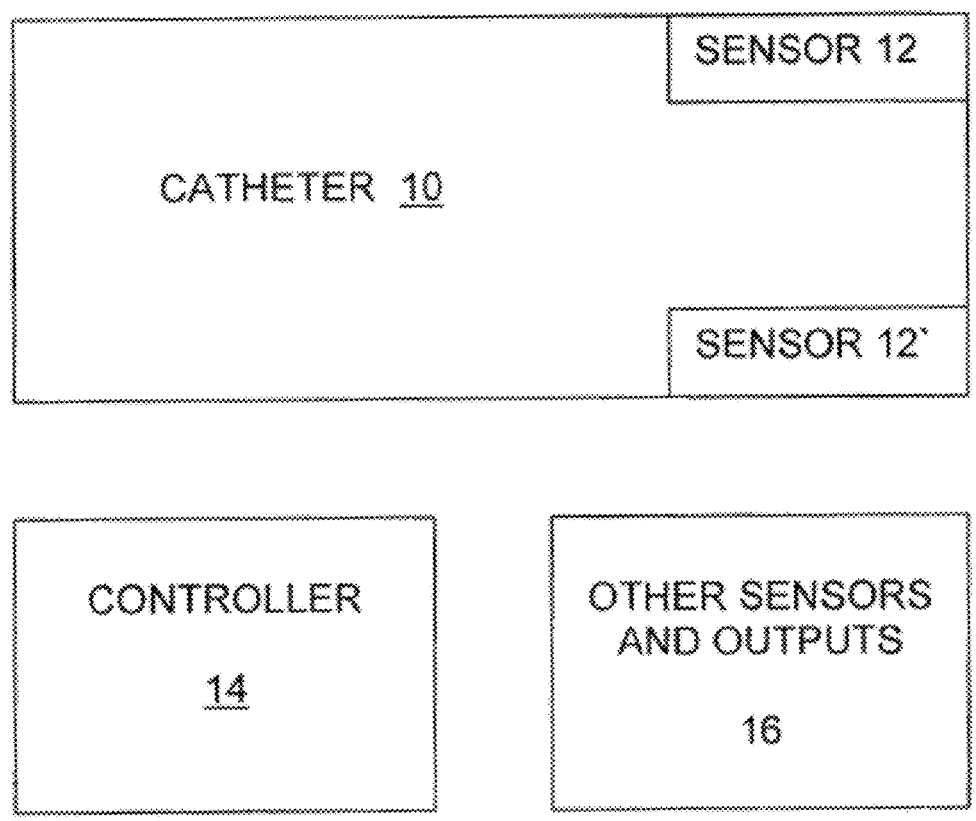
FIG. 1 is a schematic diagram showing that various sensors are used for hemodynamic optimization in combination with temperature control with an endovascular catheter.

The controller 14 may also contain the cooling or warming apparatus. Alternately, the cooling/warming apparatus may be physically separate from the controller but in electronic communication with it. Controller 14 may also allow feed in (input) from local devices that measure venous hemoglobin oxygen saturations (e.g., cerebral or muscle near infrared absorption spectroscopy devices); this is schematically represented in FIG. 1 as "other sensors and outputs 16". This may be particularly helpful for use in focal tissue therapeutics. Furthermore, the device could be coupled with measures of carbon dioxide production which reflect metabolism as well. This could include a combination of transcutaneous $CO_2$ and end-tidal $CO_2$ to produce a $CO_2$ tissue gap measurement. Other indicators of metabolic rate such as skin temperature flux, galvanic skin response, transcutaneous $PO_2$, Heart Rate Variability, transcranial Doppler, etc. could be used as well for closed loop, goal directed, and therapeutic endpoints.

Additional endpoints, such as the electroencephalogram (EEG), somatosensory evoked potential (SEP), auditory evoked potentials, and other indicators of neural activity and consciousness including those associated with sleep and attentiveness such as actigraphy, breathing rate, eye movement, and others could be used to drive temperature management to enhance sleep and optimize circadian physiology of the brain and body. These parameters have been well correlated with neurologic activity ranging from seizures to brain injury to consciousness (EEG, SEP, auditory evoked potentials) and stages of sleep (EEG, breathing rate, eye movements, actigraphy) allowing for temperature to be used to optimize ranges of neurologic activity such as sleep, seizure suppression and others.

The controller also receives and sends information to and from devices capable of changing hemodynamics. These include but are not limited to intravenous infusion systems which may provide intravenous fluids and medications capable of improving or optimizing the patient's hemodynamic and tissue perfusion status. The controller is thus operably linked directly or indirectly to other components of the system (e.g. the various devices described herein) and is capable of receiving information and data (controller input, usually in the form of e.g. measurements) from those devices. For example, the controller is configured to receive data that includes the actual values of physiological parameters of a patient. In addition, the controller is configured to receive input from an operator, e.g. a physician or health care professional, such as individual characteristics of a patient (e.g. age, weight, etc.) and desired or target values of physiological parameters for the patient. Such values may also be input from a database, e.g. a database that has stored the patient's records. The controller is also configured to calculate, for example, the difference between actual and targeted values and to generate instructions or signals which can be transmitted (output) to other devices in the system. Other devices or components of the system receive the instructions or signals as input, and the instructions cause the devices to change or maintain their operation, as necessary, in order to achieve or maintain the targeted physiological values for the patient. Any or all of these processes of data input, output, transfer, etc. may be automated, e.g. carried out by a computer or by a computer software program. For example, a computer program may be used to calculate the target values for a patient. Such programs may be linked, or a single program may be designed which encompasses and integrates all the processes and calculations.

The endovascular cooling catheter 10 can also be improved by the addition of a solid state pressure sensor 12' at its tip or other location allowing for the measurement of pressure in the inferior or superior vena cava. The combination of the pressure sensor 12' and the oximetric measurement capabilities 12 allows the catheter 10 to be used to perform goal directed therapy (GDT) simultaneously to temperature manipulation. GDT may play a critical role in optimizing global and end-organ outcomes during therapeutic temperature manipulation or vice versa.

The controller 14 could be equipped to receive information from an arterial pressure catheter 16 to include pulse pressure measurements of volume or even cardiac output measurements. Additional neurologic feedback controls such as EEG and its derivatives could be used. Heart analyses including heart rate variability could be used as an endpoint. In essence, real time physiologic variables could be used as end-points in a goal directed and closed-loop therapeutic fashion. Advanced machine learning and other techniques such as neural networks and fuzzy logic can be incorporated into developing protocols for various states (cardiac arrest, cardiogenic shock, trauma, sepsis, traumatic neurologic injury, stroke, high risk surgeries, etc.)

Closed loop cooling or heating and other resuscitation algorithms could be created allowing cooling or heating to advance based on these other measurements as targets or to indicate that hemodynamic parameters should be manipulated to optimize temperature. Such information could be provided to the controller 14 via Bluetooth or other wireless inputs. Such algorithms and feeds can be used to produce closed loop resuscitation strategies that presently include only temperature as a variable. Not only would absolute temperature endpoint tailoring be possible but other aspects of temperature change such as the rate of change could be manipulated as well by physiologic indicators. The controllers and algorithms both receive input from multiple, and sometimes unrelated, devices (such as neurologic monitoring devices, cardiovascular monitoring devices, and treatment devices) as well as send data to treatment devices (such as cardiovascular treatment devices and temperature treatment devices).

These technologies could be reduced (in size, in complexity, etc.) in the future to allow endovascular temperature manipulation through catheters placed in peripheral arm veins. Venous pressure, arterial pressure, cardiac output and oximetric information could be used in similar feedback mechanisms for external cooling methods or methods of cooling using pharmaceuticals. Examples of these might include but not be limited to cooling blankets or pads of various sources, heating pads or radiant heat sources, use of intravenous metabolic inhibitors or modulators, and the use of nasopharyngeal or other topical use of perfluorocarbon or hydrofluorocarbon evaporative or other evaporative chemistry. Noninvasive measurement of hemodynamic variables can also be used as feedback from cooling or warming using invasive cooling/warming methods.

Figure 4:
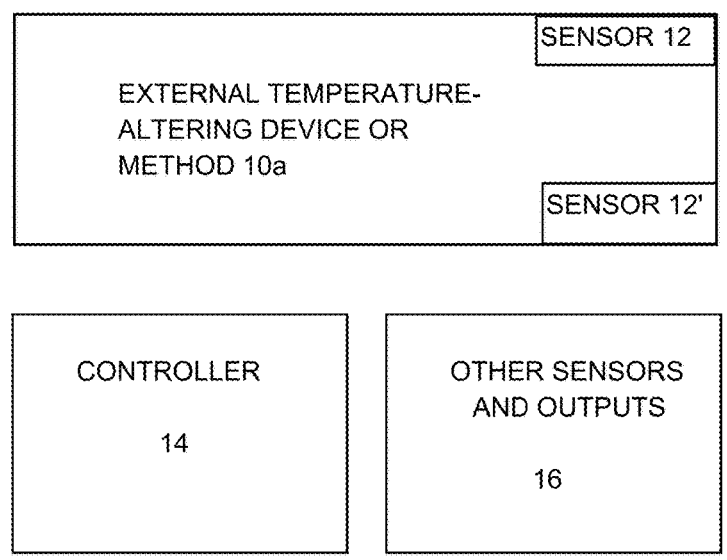
FIG. 4 is a schematic diagram similar to FIG. 1, but illustrating various sensors used for hemodynamic optimization in combination with temperature control using an external cooling device or method.
Figure 5:
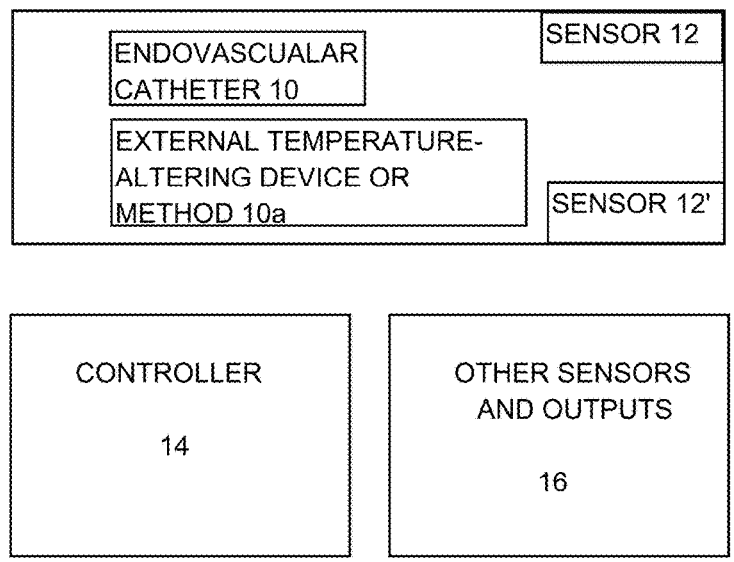
FIG. 5 is a schematic diagram similar to FIGS. 1 and 4, but illustrating various sensors used for hemodynamic optimization in combination with temperature control using both an endovascular catheter and an external cooling device or method.

To expound on the methods mentioned above, surface or external cooling, while less efficient than endovascular cooling, has advantages of technical and manual simplicity for clinical application. New engineering principles may allow for an increase in heat transfer efficiencies through such technologies as vibration and others. Regardless, a critical need still exists to allow precision use of surface or external cooling similar to endovascular cooling by guiding its application with physiologic feedback via sensor input and a control system in order to allow tailored application for therapeutic purposes. For instance, as illustrated in FIG. 4, an external temperature-altering device or method 10a may be employed as an alternative to the endovascular catheter 10 of FIG. 1. The external temperature-altering device or method may take the form of a cooling surface, a cooling blanket, a cooling pad, a cooling pillow, a cooling wrap, a cooling garment, an evaporative cooling method, or the like, and alternately or additionally, a heating surface, a heating blanket, a heating pad, a heating pillow, a heating wrap, a heating garment, or the like. Furthermore, both internal and external temperature-altering devices or methods can be used in combination, such as illustrated in FIG. 5. For instance, temperature adjustments via an endovascular catheter delivering fluid at very cold temperatures can be offset, and therefore controlled, by counter-temperature adjustments via an external heating surface.

In summary, a significant advance can be made by coupling temperature manipulation with resuscitation as a new method to optimize global and regional organ outcomes.

Controller Design

Figure 3:
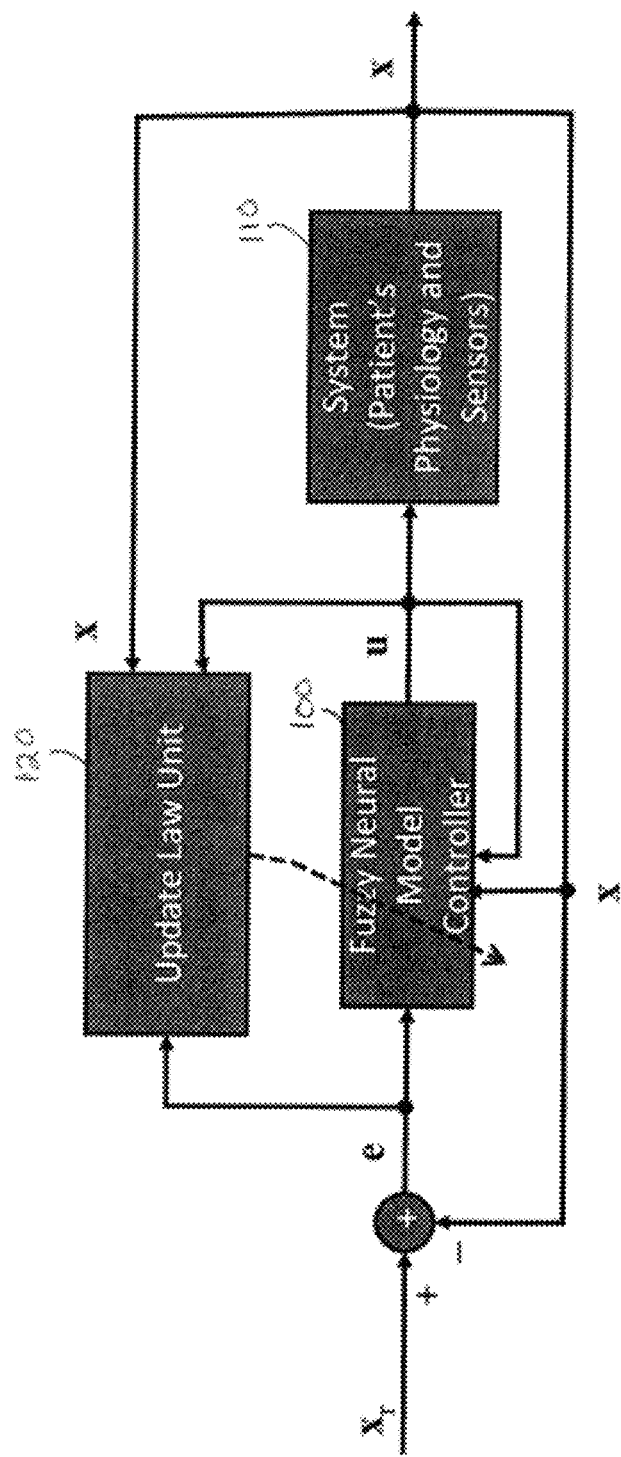
FIG. 3 is a more detailed diagram showing the controller system.

In some embodiments, the controller 14 comprises a control system, as shown in FIG. 3, which uses stable multi-input multi-output (MIMO) fuzzy neural (FN) control. The advantage of using this control system is: 1) the heuristic knowledge physicians have in treating patients, no matter how approximate and non-quantitative it might be, can be directly fed into the fuzzy neural (FN) controller and utilized towards further improvement of the system; this knowledge is then optimized by the update law unit and used directly during control processes; 2) the stability of the process is guaranteed so the patient's health is never jeopardized because of the FN controller's performance; and 3) due to the use of linguistic variables, the majority of the knowledge processed and produced by the controller is perceivable by the clinical staff. Hence the system provides some level of transparency on how it works and the results it produces. Many controllers with adaptive nature can be used for this purpose; neuro-fuzzy controllers are simply examples of such very diverse and capable controllers. In other words, while it is possible that fuzzy neural models would be among more suitable solutions, there are a multitude of other controllers such as optimal controllers, H-Infinity (robust) controllers, linear adaptive controllers, neural (non-fuzzy) controllers, PID controllers, and model-based controllers, which can be effectively used for this problem.

The main variables of the control system shown in FIG. 3 are as follows:

$x_r(t)=[x_{r1}(t) \ldots x_{rn}(t)]$ is the multi-dimensional reference (desired) vector that identifies the desired values for the hemodynamic parameters and other physiological signals monitored and controlled throughout the process, i.e. $x_{r1}(t)$=oxygen extraction ratio, $x_{r2}(t)$=desired central venous pressure, $x_{r3}(t)$=desired transcutaneous $CO_2$, $x_{r4}(t)$=desired end-tidal $CO_2$, $x_{r5}(t)$=desired skin temperature flux, $x_{r6}(t)$=desired tissue hemoglobin oxygen saturation $x_{r7}(t)$=desired variations in heart rate variability, and so on. These values are set by physicians and may change from one patient to another and even for a given patient throughout the course of TH.

$x(t)=[x_1(t) \ldots x_n(t)]$ is the multi-dimensional output state vector reflecting the actual value of the monitored hemodynamic and other physiological signals, i.e. $x_1(t)$=actual oxygen extraction ratio, $x_2(t)$=actual central venous pressure, $x_3(t)$=actual transcutaneous $CO_2$, $x_4(t)$=actual end-tidal $CO_2$, $x_5(t)$=actual skin temperature flux, $x_6(t)$=actual tissue hemoglobin oxygen saturation, $x_7(t)$=actual variations in heart rate variability, and so on. These values are measured by the sensors described above.

$u(t)=[u_1(t) \ldots u_k(t)]$ is the multi-dimensional control input generated by the FN controller that is used to force the monitored physiological measures to follow/reach the desired values. Specifically: $u_1(t)$=temperature of endovascular catheter, $u_2(t)$=volume of fluids given to patient, and so on. These values are measured by the sensors described and are calculated and updated by the FN controller.

$e(t)=[e_1(t) \ldots e_k(t)]$ is the error signal that is the difference between the desired and actual hemodynamic parameters as well as other physiological signals, as described above. This error signal is used to create the control input and to update the control law, as shown in the schematic diagram of FIG. 3.

The main components of the control system shown in FIG. 3 are as follows:

Fuzzy Neural Model Controller 100 accepts as input the error signal, the actual state signal (x) and the control input in the previous steps (e.g. previous or initial settings, instructions or operating parameters for the devices) and generates the control input for the next step (e.g. recommended future or next settings instructions or operating parameters for the devices). The fuzzy structure of the neural model used in the FN controller also provides the capability of incorporating physicians' heuristic knowledge into the control input model since the model uses linguistic variables.

System 110 that includes patient's physiology and sensor sets responds to the control inputs such as the endovascular temperature and volume of fluid, and shows its response in the form of changes in the values of hemodynamic parameters and other physiological signals.

The above-mentioned system is a time varying one as the patient's exact physiology undergoes settled changes throughout the treatment process. This requires updating of the model as well as the control law. This is done by the update law unit 120, which updates the model estimated from the system based on the latest observations from the system.

While various embodiments have been described herein, it will be understood by persons of ordinary skill in the art that changes may be made to the described embodiments that are still within the scope of the appended claims, and aspects of the various disclosed embodiments can be combined with one another and also still be considered within the scope of the appended claims.

What is claimed is:

1. A system for performing therapeutic hypothermia, comprising:
a controller;
one or more sensors and devices for at least one of measuring or adjusting hemodynamic parameters;
at least one of a group of an external pulse oximeter or an indwelling arterial catheter capable of continuous blood gas measurements;
an endovascular catheter providing oximetric values, wherein said one or more sensors and devices, and said endovascular catheter, are operatively controlled by said controller; and
said external pulse oximeter or said indwelling arterial catheter providing oxygen saturation data combinable with the oximetric values from the endovascular catheter to determine an oxygen extraction ratio (OER), the controller being operable to control the endovascular catheter to regulate temperature control based on the determined OER.

2. The system of claim 1 wherein one or more of said one or more sensors and devices and said endovascular catheter are connected with said controller by wireless communication.

3. The system of claim 1, wherein said controller comprises one of a group of a stable multi-input multi-output (MIMO) fuzzy neural model controller, an optimal controller, an H-Infinity (robust) controller, a linear adaptive controller, a neural (non-fuzzy) controller, a PID controller, and a model-based controller.

4. The system of claim 1, wherein said controller is configured to receive and process one or more of: desired values of hemodynamic and physiological parameters for a patient; actual values of hemodynamic and physiological parameters for said patient; error signals; and heuristic knowledge.

5. The system of claim 1, wherein said system further comprises an update law unit.

6. The system of claim 1, further comprising external means for cooling or warming said patient.

7. The system of claim 6, wherein said external means includes heating or cooling pads as alternative to or adjuncts to endovascular temperature methods.

8. The system of claim 1, wherein said one or more sensors and devices include an intravenous infusion system.

9. The system of claim 8, wherein said intravenous infusion system is a medication or fluid delivery intravenous infusion system.

10. The system of claim 1, further comprising an external temperature-altering device including at least one of a cooling surface, a cooling blanket, a cooling pad, a cooling pillow, a cooling wrap, a cooling garment, an evaporative cooling method, a heating surface, a heating blanket, a heating pad, a heating pillow, a heating wrap, or a heating garment.

11. The system of claim 1, wherein the one or more sensors and devices for at least one of measuring or adjusting hemodynamic parameters includes sensors of at least one of a group including neural activity, consciousness, circadian physiology, and attentiveness.

12. A method of performing therapeutic temperature management, comprising:
measuring and adjusting hemodynamic parameters in a patient;
determining an oxygen extraction ratio (OER) using oximetry values from an endovascular catheter and arterial saturation data provided by one of an external pulse oximeter or an indwelling arterial catheter capable of continuous blood gas measurement; and
adjusting temperature in said patient using at least one of an internal temperature-altering device or external temperature-altering device, based on the OER.

13. The method of claim 12, wherein the internal temperature-altering device includes an endovascular catheter.

14. The method of claim 12, wherein the external temperature-altering device includes at least one of a cooling surface, a skin cooling pad, a cooling blanket, a cooling pad, a cooling pillow, a cooling wrap, a cooling garment, an evaporative cooling method, a heating surface, a skin heating pad, a heating blanket, a heating pad, a heating pillow, a heating wrap, or a heating garment.

15. The method of claim 12, wherein said measuring and adjusting includes measuring one or more of vascular pressure and oximetric measurements.

16. The method of claim 15 wherein said measuring and adjusting includes measuring one or more of central venous hemoglobin saturation, central venous pressure, oxygen extraction ratio, pulse oximetry, transcutaneous $CO_2$ end-tidal $CO_2$ skin temperature flux, galvanic skin response, transcutaneous $PO_2$ variations of Heart Rate Variability, cardiac output, stroke volume variation, pulse volume variation, central venous pressure, tissue hemoglobin oxygen saturation, cerebral hemoglobin oxygen saturation, EEG, transcranial Doppler, somatosensory evoked potential, breathing rate, auditory evoked potentials, actigraphy, and eye movement.

17. The method of claim 15 wherein the measured and adjusted variables are correlated to a state of precision and optimized physiologic endpoints including at least one of a group comprising metabolism, cardiovascular function, and at least one neurologic state.

18. The method of claim 12 further comprising the step of controlling one or more of a skin heating pad or a skin cooling pad.

19. The method of claim 12 wherein said measuring and adjusting includes measuring and adjusting one or more of central venous hemoglobin saturation, central venous pressure, oxygen extraction ratio, pulse oximetry, transcutaneous $CO_2$ end-tidal $CO_2$ skin temperature flux, galvanic skin response, transcutaneous $PO_2$ variations of Heart Rate Variability, cardiac output, stroke volume variation, pulse volume variation, central venous pressure, tissue hemoglobin oxygen saturation, cerebral hemoglobin oxygen saturation, EEG, and transcranial Doppler.

\* \* \* \* \*

UNITED STATES PATENT AND TRADEMARK OFFICE
CERTIFICATE OF CORRECTION

PATENT NO. : 10,307,288 B2
APPLICATION NO. : 15/307690
DATED : June 4, 2019
INVENTOR(S) : Kevin Ward et al.

It is certified that error appears in the above-identified patent and that said Letters Patent is hereby corrected as shown below:

On the Title Page

At item (71), Lines 1-5, "Hasan Alam, Ann Arbor, MI (US); Kevin Ward, Superior Township, MI (US); Kyle Gunnerson, Saline, MI (US); Kayvan Najarian, Northville, MI (US)" should be --THE REGENTS OF THE UNIVERSITY OF MICHIGAN, Ann Arbor, MI (US)--

Signed and Sealed this
Second Day of July, 2019

Andrei Iancu
*Director of the United States Patent and Trademark Office*